United States Patent [19]

Schilling et al.

[11] Patent Number: 5,178,674
[45] Date of Patent: * Jan. 12, 1993

[54] ACCELERATORS FOR CATIONIC AQUEOUS BITUMINOUS EMULSION-AGGREGATE SLURRIES

[75] Inventors: Peter Schilling; Hans G. Schreuders, both of Charleston, S.C.

[73] Assignee: Westvaco Corporation, New York, N.Y.

[*] Notice: The portion of the term of this patent subsequent to Mar. 17, 2009 has been disclaimed.

[21] Appl. No.: 819,084

[22] Filed: Jan. 9, 1992

[30] Foreign Application Priority Data

Apr. 11, 1990 [EP] European Pat. Off. ........ 90401001.4

[51] Int. Cl.⁵ .............................................. C08L 95/00
[52] U.S. Cl. ..................................... 106/277; 106/280
[58] Field of Search .......................... 106/246, 277, 280

[56] References Cited

U.S. PATENT DOCUMENTS 5,096,495 3/1992 Schilling et al. .................... 106/277

*Primary Examiner*—David Brunsman
*Attorney, Agent, or Firm*—Terry B. McDaniel; Daniel B. Reece, IV; Richard L. Schmalz

[57] ABSTRACT

Compositions of matter are disclosed which act as cure rate accelerators for bituminous emulsion-aggregate slurries which compositions are formed as the reaction products of an excess of polycarboxylic acid with a polyamine selected from fatty amines, fatty propane diamines, fatty amidoamines, and fatty imidazolines.

3 Claims, No Drawings

ACCELERATORS FOR CATIONIC AQUEOUS BITUMINOUS EMULSION-AGGREGATE SLURRIES

This application is a continuation-in-part of co-pending application Ser. No. 07/446,809 filed Dec. 6, 1989, now U.S. Pat. No. 5,046,495, which is a divisional of application Ser. No. 07/322,916, filed Mar. 14, 1989, now abandoned.

BACKGROUND OF THE INVENTION

(1) Field of the Invention

The present invention relates to mixing-grade, quick-setting cationic aqueous bituminous emulsion-aggregate paving slurry seal mixtures. More particularly, this invention relates to said paving slurry seal mixtures formed with cationic emulsions prepared by emulsifying bitumen, such as an asphalt, in water with a cation-active emulsifier which is the product of the reaction of polyamines with certain polycarboxylic acids and containing accelerators to shorten the curing time at below 75° F. The accelerators are modified nitrogen-containing tall oil fatty acids.

(2) Description of the Prior Art

Conventionally, emulsion slurry seals are formulated from (1) mineral aggregate which is a fine stone aggregate and/or mineral filler and (2) about 15% to about 25% by weight thereof of a mixing-grade, slow-setting emulsion containing from about 50% to about 75% by weight of bituminous residue (usually asphalt), with a further addition of about 5% to about 25% of water, based on the weight of the dry aggregate, to attain slurry consistency. Usually, densely-graded aggregates, such as granite screenings, limestone screenings, dolomite screenings and blast furnace slag, are combined with bituminous emulsions to produce slurry seal compositions. These aggregates range in size from anything passing all through a sieve of No. 4, and even No. 10 mesh, with from 15% to 20% passing through as fine a mesh as 200 mesh, as described in ASTM C136.

The advent of slurry seal as a paving and road maintenance technique was first developed for use with anionic aqueous bituminous emulsions. A slurry seal is an intimate mixture of emulsified bituminous material and fine-grained aggregate held in suitable suspension until applied to the road surface. The slurry seal emulsion must be of an oil-in-water type. In such a mixture with aggregate, the aqueous emulsion form of the bituminous material has been generally preferred because it is less hazardous and more economical to use than hot mix or cutback (solvent containing) asphalts. Further, the aqueous emulsion form can be stored, transported and applied at much lower temperatures, obviating the necessity of heating equipment to maintain a bitumen-aggregate system in a workable or usable form. While these advances have been recognized, widespread acceptance has not been achieved due to disadvantages found in previous aqueous bituminous emulsions.

More recently, cationic bituminous emulsions have come into use and eliminate many of the disadvantages of the anionic emulsions. Bituminous emulsions formulated using cationic emulsifiers do not "break" in the same manner as anionic emulsions, but rather the bituminous material is deposited from the emulsion due to the attraction of polar charges between the bituminous droplets and negatively charged aggregate surfaces. Thus, cationic bituminous emulsions deposit more rapidly than the anionic bituminous emulsions on aggregate surfaces and are bonded to the aggregate by the electrostatic action at the interface of the bitumen and the aggregate material, The aqueous cationic bituminous emulsions themselves are relatively stable, and the emulsion stability may be enhanced by various additives well known in the art. Most cationic bituminous emulsions, however, deposit on the surface of aggregate materials rapidly when aggregate is contacted with the emulsions. Bitumen from an aqueous cationic bituminous emulsion is deposited from the emulsion due to the charge attraction between the bituminous droplets and the aggregate materials. The rapid setting action of cationic bituminous emulsions is of considerable ;advantage in road building, such as seal coats, since the roads can be opened to traffic shortly after application of the coating. Although the rate of asphalt deposition, for example, from the emulsion can be controlled to some extent, the time required for complete deposition is never very long and it is therefore the practice to combine the cationic emulsion with the aggregate at the site of road construction, either on the surface of the road itself, or in a mobile mixer which permits the emulsion aggregate mix to be rapidly spread. Due to the charge attraction mechanism, the rapidity of deposition of bituminous materials from the cationic emulsion is closely related to the generally negatively charged surface area of the aggregate or filler material. Thus, while a specific cationic bituminous emulsion might provide suitable properties for use in conjunction with some aggregates, the same cationic emulsion may not exhibit suitable properties when used with very finely ground materials having vastly larger total surface area. The rapid deposition characteristics of the cationic bituminous emulsions frequently makes it impossible to use such emulsions with fine-grained aggregate in slurry form such as in gun application or spreader box application. Therefore, since the slurry seal should mix well, pump well, lay down well, not stiffen while being applied, and, after setting, wear well under traffic, it is particularly desirable to be able to control the setting time of the slurry for various aggregates employed.

Acidified reaction products of the above described polycarboxylic acids, anhydrides, sulfonated fatty acids and epoxidized glycerides with certain polyamines are suitable emulsifiers yielding asphalt emulsions which can be mixed with fine grained aggregate to give workable aggregate/emulsion mixes.

These emulsifiers generally are disclosed in U.S. Pat. No. 4,447,269 to Schreuders, et al., U.S. Pat. No. 4,450,011 to Schilling, et al., U.S. Pat. No. 4,547,224 to Schilling, et al., U.S. Pat. No. 4,462,890 to Schilling, et al., U.S. Pat. No. 4,464,286 to Schilling; and U.S. Pat. No. 4,597,799 to Schilling.

However, the mixing performance is in many cases dependent on the source and type of the aggregate and asphalt used for emulsification. Also, climatic conditions play a major role in slurry seal application. Hot weather makes it more difficult to mix, and slurry seal will cure much faster to gain the necessary strength for rolling traffic, Low temperatures provide good mixing conditions, but the times required for slurry curing are longer than desired Optimum formulations of slurry seal mixes provide mixing times long enough to ensure uniform mixes and, after placement on the road surface, cure fast enough to allow for quick re-opening to rolling traffic.

Accordingly, an object of this invention is to provide novel types of curing accelerators which in the presence of inorganic fillers, such as Portland cement, will reduce the time of the slurry to gain cohesive strength rapidly.

A further object of this invention is to provide a novel mixture of aggregate and bituminous emulsion.

A further object is to provide a mixture of the above character which is workable under a broad range of conditions. Another object is to provide a mixture of cationic bituminous emulsion and aggregate whose setting time can be varied.

A particular object is to provide an aqueous bituminous emulsion fine-grained aggregate slurry mixture which deposits at a fairly rapid rate after being applied to the surface to be treated, and is usable for a longer period of time to enable application in slurry form.

SUMMARY OF THE INVENTION

The above objectives are met in the improved cationic aqueous bituminous emulsion-aggregate slurries formed by combining prewet aggregate with cationic emulsions prepared by emulsifying bitumen, such as an asphalt, in water with cationactive emulsifier which is the product of the reaction of a polyalkylene amine, with a polycarboxylic acid and anhydrides of the general formulae

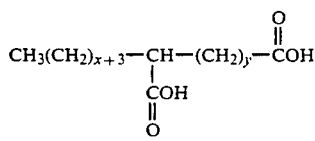

or

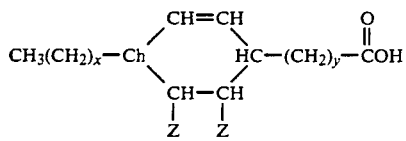

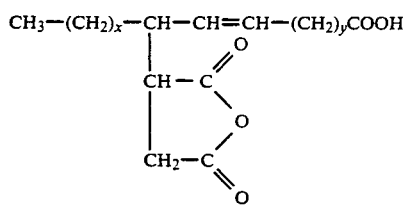

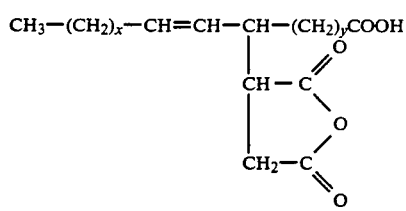

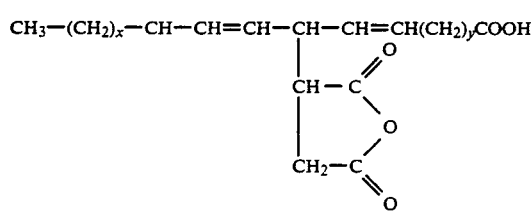

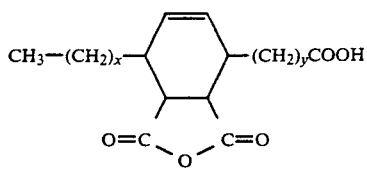

wherein x and y are integers from 3 to 9, x and y together equal 10-14, at least one Z is a carboxylic acid group and any remaining Z is hydrogen, wherein the improvement comprises adding to the aggregate prewet water from 0.02% to 0.07%, based on aggregate, of one or more accelerators as herein described.

Additional emulsifiers used in this invention are reaction products of these polyamines with sulfonated fatty acids, with resin acids (rosin) reacted with maleic anhydride or fumaric acid, and epoxidized esters of unsaturated fatty esters such as tallates, oleates, linoleates, and glycerides such as vegetable oils and animal fats. Examples of such reactants include:

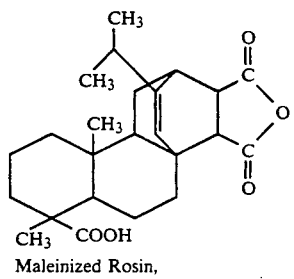

Maleinized Rosin,

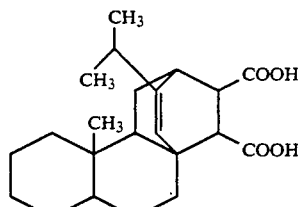

Fumarized Rosin, and

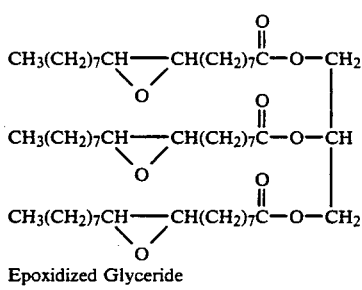

Epoxidized Glyceride

Accelerators of the invention, added in small amounts to the pre-wet water, which in the presence of inorganic fillers such as Portland cement shorten the cure times, are fatty acids, the polycarboxylic acids as shown above, and preferentially reaction products obtained by reacting these polycarboxylic acids with small amounts of polyalkylene amines to increase the molecular weight. Also, fatty amines, fatty propane diamines, fatty amido amines and fatty imidazolines reacted with excess of the polycarboxylic acids shown above will result in accelerators.

DESCRIPTION OF THE PREFERRED EMBODIMENTS

A typical cationic aqueous bituminous emulsion aggregate slurry is formulated in the laboratory with an amount of aggregate pre-wetted with water and mixed with a suitable cationic bituminous emulsion to a desired consistency. Suitable consistency is obtained by using mixed gradations of aggregates forming a smooth non-separating uniform mixture of cationic aqueous bituminous emulsion-aggregate which can be evenly spread onto an existing surface The ultimate toughness of the applied slurry is obtained as the bitumen, such as asphalt, deposits on the aggregate particles and binds the newly applied coating to the pre-existing surface as a mixture of asphalt cement and aggregate.

As a paving technique at the roadsite, a mobile self-propelled unit capable of uniformly metering the aggregate, water, inorganic or organic additive and emulsion components may be used. A typical unit is equipped with separate tanks for aggregate, water, additive and emulsion which are continually metered into a mixing chamber at a pre-determined ratio. The continually fed components are retained in the mixing chamber for approximately one minute and then fed into a spreader box and applied to the surface to be coated. Batch operated pneumatic devices can also be used for suitable placement of the cationic bituminous aggregate slurries of this invention.

The slurry of this invention broadly comprises aggregate and a bituminous emulsion made up of bitumen, water and as cationic emulsifier, the reaction product of a modified polyamine and a polycarboxylic acid and an accelerator to shorten curing time as described above in the Summary of Invention.

When the emulsifiers are the reaction products of the modified polyamines with sulfonated carboxylic acids derived by sulfonation of tall oil fatty acid and oleic acid, the sulfonated products are characterized by an acid number from about 220 to 330, saponification number from about 300 to 360.

Sauls and Ruggenberg disclose the sulfonation of oleic acid with sulfur trioxide in liquid sulfur dioxide in U.S. Pat. No. 2,743,288.

Pugh and Chesworth disclose in British Pat. No. 1,278,421 the sulfonation of oleic acid with gaseous sulfur trioxide diluted with an inert gas with a continuously formed liquid film of the unsaturated fatty acid.

The sulfonation of tall oil fatty acid is also disclosed in the above mentioned patents. Because of the complexity of the composition of tall oil fatty acids, no attempt to identify the sulfonated products was made.

Reaction mechanism and all aspects of sulfonation are reviewed in E. E. Gilbert, "Sulfonation and Related Reactions," R. E Krieger Publishing Company, Huntington, N.Y., 1977.

The above $C_{21}$-dicarboxylic acid and $C_{22}$-carboxylic acids or anhydride as well as the fumarized or maleinized rosins have carboxylic acid (or anhydride) functions which differ in their reactivity towards amines or polyamines. For example, the carboxyl group in $C_{21}$-dicarboxylic acid connects so the six membered ring system is more shielded and less reactive than the terminal carboxyl group In the case of $C_{22}$-tricarboxylic acid or anhydride and fumarized and maleinized resin acids, the carboxyl groups introduced by condensation with maleic anhydride or fumaric acid are more reactive than the original carboxyl groups of the unsaturated fatty acids and resin acids. They will react at the lower temperature and can be selectively amidated, when less than the equimolar amounts of amine are used.

The reaction products of $C_{21}$-dicarboxylic acid and $C_{22}$-tricarboxylic acid (anhydride) with aminoethylpiperazine, the invention curing accelerators, are described as follows:

Novel compositions of matter result from the reaction of aminoethylpiperazine and $C_{22}$-tricarboxylic acid in a molar ratio of from 0.5:1 to 1:1, respectively.

When one mole cf $C_{22}$-tricarboxylic acid is reacted with 0.5 mole of aminoethylpiperazine, two molecules of tricarboxylic acid will be interlinked via an aminoamido bridge resulting in a higher molecular weight aminoamidoimido tricarboxylic acid (I).

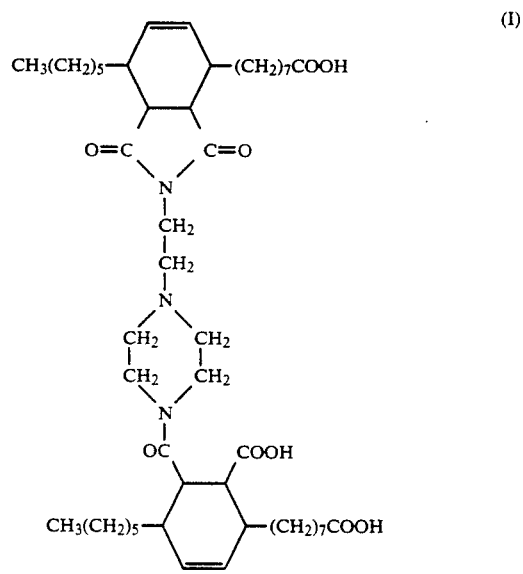

By using one mole of aminoethylpiperazine per one mole of $C_{22}$-tricarboxylic acid and reacting between 120° and 150° C., the aminoimido carboxylic acid (II) will be formed predominately.

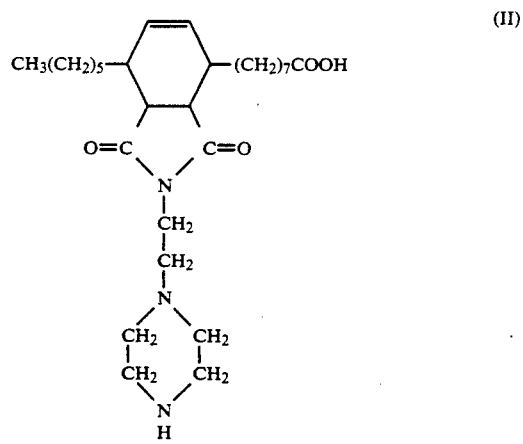

Increasing the temperature to 180°–230° C. will result in the formation of a polyamidoimido amine, as a result of the condensation of the secondary amine group with the terminal carboxyl group.

Using two moles of aminoethylpiperazine per mole of C$_{22}$-tricarboxylic acid will predominantly result in a mixed amino amido and aminoimide of the tricarboxylic acid (III) when heated to 220°-240° C.

By reacting one mole C$_{21}$-dicarboxylic acid with 0.5 mole or one mole aminoethylpiperazine, the dicarboxylic acid (V) and aminomonocarboxylic acid (VI), respectively, are formed.

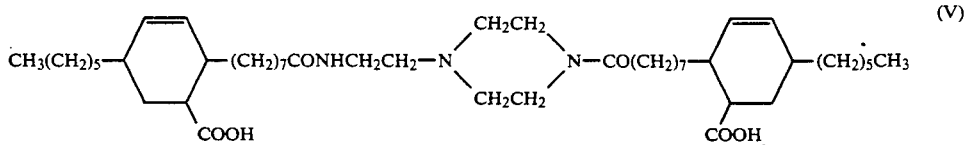

(V)

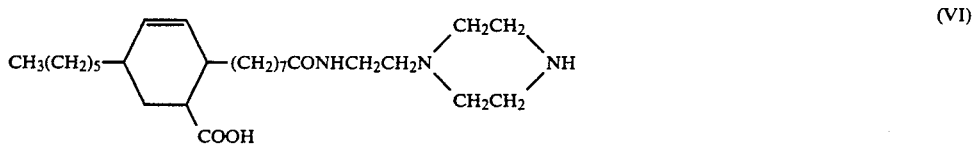

(VI)

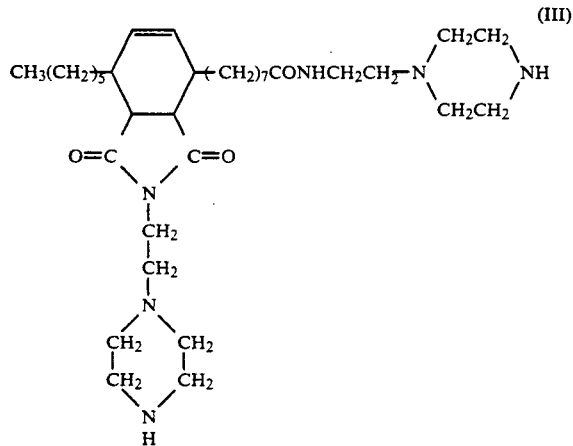

(III)

Increasing the amount of aminoethylipiperazine to three moles or more per one mole C$_{22}$-tricarboxylic acid will yield the triamido amine (IV) when heated to 220°-240° C.

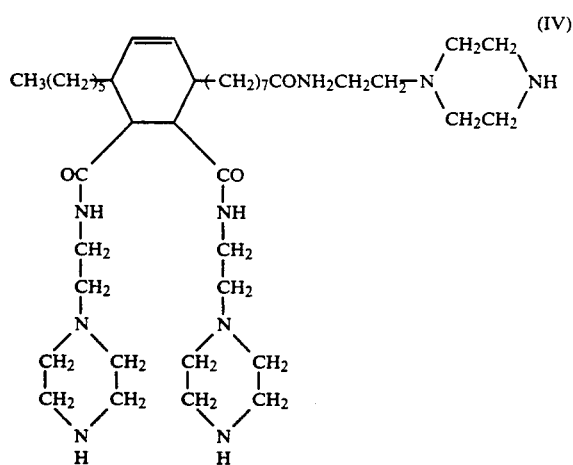

(IV)

These formulae represent the ideal cases. In reality the reaction products will represent mixtures of the products shown above.

Novel compositions also result from the reaction of aminoethylpiperazine and C$_{21}$-dicarboxylic acid in a molar ratio of from 0.5:1 to 1:1, respectively.

The products I, II,.V, VI when introduced as the sodium or potassium salt into the emulsion aggregate slurry will act as accelerators, whereas the products III and IV and the corresponding diamidoamine of C$_{21}$-dicarboxylic acid, when acidified with an inorganic acid in water, are emulsifiers for asphalt.

The above scheme only depicts possible examples derived by using one specific polyamine.

Other polyamines suitable as precursors are those which are able to form imidazolines or amidoamines with carboxylic acids such as ethylene diamine, diethylene triamine, triethylene tetramine, tetraethylene pentamine, pentaethylene hexamine, and higher homologues; N-aminoethyl propane diamine, N,N'-diaminoethyl propane diamine and the N-aminoethyl- or N,N'-diaminoethyl-substituted butane diamines, pentane diamines and hexane diamines, and N-hydroxyethyl ethylene diamine. These compounds have the general formula

H$_2$NCH$_2$CH$_2$NHR

R=H—, CH$_3$—, C$_2$H$_5$—, C$_3$H$_7$—, —CH$_2$CH$_2$OH, —(CH$_2$CH$_2$NH)$_x$H x=1, 2, 3, 4, . . . 10 or, R$_1$R$_2$N(CH$_2$)$_y$NHR$_3$

R$_1$=H—, CH$_3$—, C$_2$H$_5$—, NH$_2$CH$_2$CH$_2$—,

R$_2$=H—, CH$_3$—, C$_2$H$_5$—,

R$_3$=H—, CH$_3$—, C$_2$H$_5$—, C$_3$H$_7$—, NH$_2$CH$_2$CH$_2$—, y=2, 3, 4, 5, 6.

Amines capable of forming amidoamines but not imidazolines are: 1,3-diaminopropane, 1,4-diaminobutane, 1,5-diaminopentane, 1,6-diaminohexane, piperazine (1,4-diazacyclohexane), N-aminoethylpiperazine, N-hydroxyethyl piperazine, N-aminopropyl-propane diamine-1,3, N-methyl-N-aminopropylpropane diamine-1,3, N-aminohexylhexane diamine-1,6.

In addition, polyamines containing other functionalities such as (—O—), thioether (—S—), sulfoxide (—SO—), sulfone (—SO$_2$—) groups, as well as aromatic structures are also suitable for condensation.

R$_1$H$_2$N(CH$_2$)$_x$Y(CH$_2$)$_z$NH$_2$

Y = O, S, SO, SO$_2$, C$_6$H$_4$ x = 2-10 z = 2-10

Further modifications of the above described aminoimides (I) or aminoamides (II, VI) are their reaction products with reactive oxirane systems such as ethylene oxide, propylene oxide or butylene oxide. The reaction products belong to the class of N-hydroxyethyl-, N-2-hydroxypropyl- and N-2-hydroxy butyl -amino amidoamines. If excess oxirane is reacted, polyethylene oxides, polypropylene oxides or polybutylene oxides are obtained. The hydroxyl groups will also react in this case.

Another modification may involve the use of an alkylating agent such as methyl-, ethyl-, or benzyl halides, sulfates, phosphates, etc. The resulting compounds are classified as mono-, di-, or triquaternary ammonium salts.

Another method to synthesize curing accelerators is to react a polyamine such as aminoethylpiperazine or diethylene triamine with aliphatic or aromatic carboxylic or polycarboxylic acids and react these products with $C_{21}$-dicarboxylic acids, $C_{22}$-tricarboxylic acid (or anhydride) or fumarized and maleinized resin acids (rosin). Also, fatty primary and secondary amines as well as fatty propane diamines reacted with the above carboxylic acids will give accelerators. Some of the structures obtained with $C_{22}$-tricarboxylic acid are shown below:

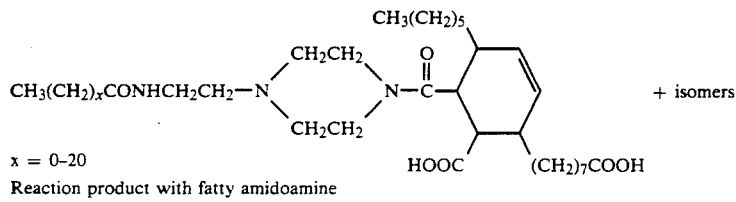

x = 0–20
Reaction product with fatty amidoamine

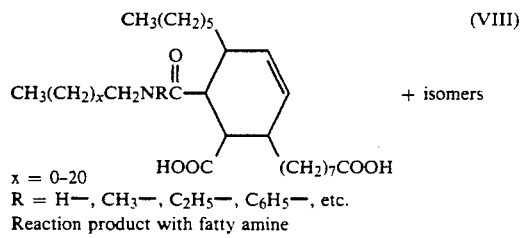

x = 0–20
R = H—, CH₃—, C₂H₅—, C₆H₅—, etc.
Reaction product with fatty amine

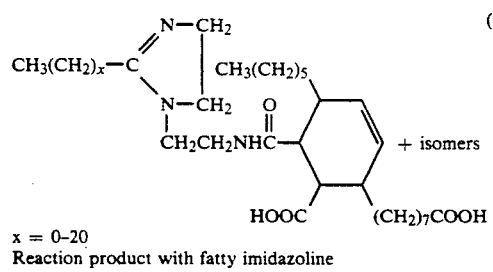

x = 0–20
Reaction product with fatty imidazoline

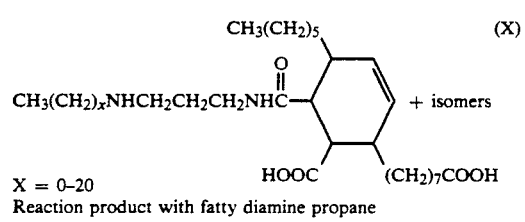

X = 0–20
Reaction product with fatty diamine propane

The use of the modified $C_{19}$-, $C_{21}$-, $C_{22}$-polycarboxylic acid and anhydrides as well as the maleinized or fumarized (rosin) resin acids, sulfonated fatty acids or epoxidized saponified glycerides or esters as cure accelerators for cationic slurry seal applications was heretofore unknown.

The examples which follow are illustrative of accelerators which when incorporated into slurry seal formulations allow mixing under shear with a variety of siliceous and calcareous aggregates and rapid curing of these mixes at temperatures below 75° F.

In preparing the bituminous emulsions employed in the invention paving slurry seal mixtures, an aqueous acidic solution of the emulsifiers described below is intimately mixed under high shear in a colloid mill. The bitumen content can range from 30% to about 80% by weight, preferably between 60% and 70%. The dosage of the emulsifier can range from 0.1–10% by weight of the emulsion, preferably between 0.5–2% by weight of the emulsion. Dependent on the emulsifier, a slurry grade emulsion is obtained in a pH range of 2–7, with the optimum performance at a pH of about 2.5.

The "bitumen" used in the emulsion may be derived from domestic or foreign crude oil; it also includes bitumen, natural asphalt, petroleum oil, oil residue of paving grade, plastic residue from coal tar distillation, petroleum pitch, and asphalt cements diluted from solvents (cutback asphalts). Practically any viscosity or penetration graded asphalt cement for use in pavement construction as described in ASTM designation D-3381 and D-946 may be emulsified with the aid of the emulsifiers of this invention.

The cationic soap solutions are normally obtained by suspending the amidoamine or imidazoline in water to which a sufficient amount of a suitable acid, for instance, hydrochloric, sulfuric, and phosphoric acid or the like is added until the desired pH value below 7 is reached and a clear emulsifier solution is obtained. Thereafter, the soap solution which is preheated to 55° C. and the fluid asphalt which is preheated to 120°–125° C. are mixed under high shear in a colloid mill to give asphalt emulsions of brown color and creamy texture. Prior to testing according to ASTM D-244, the emulsions are stored at 70° C. for 16 hours.

The aggregates of the invention paving slurry seal mixtures are densely graded aggregates which range in size from anything passing through a No. 4 sieve and at least 80% retained on 200 mesh.

Aggregate mixing tests are performed by mixing the aggregate with water and aqueous bituminous emulsion. An inorganic additive-mineral filler, such as Portland cement, hydrated lime, limestone dust and fly ash, may be added to accelerate set/break time and organic salts, such as ammonium sulfate, or emulsifiers may be added to retard the set/break or organic additives, such as disclosed in this invention, to accelerate the set/break of the slurry system. Such additives shall comply with the requirements of ASTM D-242. The materials are mixed in a mixing bowl until a homogeneous slurry mixture is obtained. The inability to form a stable slurry within 30 seconds of mixing time when proper proportions of each ingredient are used would indicate a mixture in which the materials are not compatible. This mix design is necessary to simulate field conditions, After the slurry is mixed, it is spread in a mold which is placed on an asphalt felt, and the set/break time is measured by blotting the exposed slurry surface with a paper rowel, the slurry is considered to be "set." The cure time could also be measured with a cohesion testing device. Many other tests such as described in ASTM D-3910 are used to measure strength and other physical properties of slurry. The Performance Guide for Slurry Seal published by the Asphalt Emulsion Manufacturers Association is used to measure the performance of the slurry seal.

The emulsion should be stable during mixing and should set within the designed time period following application. The emulsifiers used in this invention perform very satisfactorily without auxiliary emulsifiers. For instance, the setting times can be controlled with the concentration of emulsifier, the addition of lime, cement or other inorganic additive and the invention accelerators, which would alter the break characteristics of the slurry system. An organic additive-polymer latex may also be employed to strengthen the matrix. The organic polymer additive is preferably added to the emulsion-aggregate slurry; the curing accelerator is added to the pre-wet water in the form of an alkali metal salt.

Either a mixture of tall oil fatty acids, preferably tall oil pitch, can be added to the bitumen (asphalt) prior to emulsification to improve break or improve the viscosity of the emulsion, or blends of the above described amidoamines with compatible cationic or nonionic emulsifiers may be used for the emulsification of the bitumen. Auxiliary emulsifiers, which may constitute up to 90% of the total combined emulsifier formulation, are fatty amines, fatty propane diamines, fatty amidoamines, and fatty imidazolines. Others are fatty monoquaternary ammonium salts and fatty diquaternary diammonium salts and nonionic emulsifiers, such as ethylene glycol polyethers of nonyl- or dodecyl phenol, Combinations of fatty monocarboxylic acids, of various sources and the $C_{19}$- and $C_{21}$-dicarboxylic acids or $C_{22}$-tricarboxylic acid or anhydrides can also be used for the preparation of the emulsifiers as well as the accelerators. Monocarboxylic acids suitable for this purpose are tall oil fatty acids, crude tall oil, rosin acids, tall oil pitch, tallow fatty acids, soya fatty acids and the like. Kraft lignin, oxidized lignin, desulfonated sulfite lignin or VINSOL may also be co-reacted to yield modified emulsifiers.

Dimer acids, which are long chain $C_{36}$-aliphatic carboxylic acids obtained by dimerization of fatty acids of various sources, may be also co-reacted. An example of this type of acid is produced by Emery Industries, Inc. under the trade name "Empol ® Dimer Acids."

In a similar way, blends of sulfonated fatty acids as well as fumarized or maleinized rosin (resin acids) or epoxidized glycerides or other esters, with the above described co-reactants (fatty acids, oils, fats, lignins, VINSOL, dimer acid) can be reacted with the polyamines to give combinations of polyamidoamine emulsifiers and amino carboxylic acid accelerators.

The emulsions prepared with the polyaminoamide condensates are stable and can be stored for a long period of time until required for use. The cationic aqueous bituminous emulsions employed in the invention slurries are slow-setting at temperatures below 75° F., However, the set time may be shortened by adding lime or cement and the invention modified carboxylic acid alkaline earth salts or soaps of fatty acids, rosin acids and the modifications thereof with fumaric acid, acrylic acid or maleic anhydride, providing an emulsion with quick-setting characteristics.

GENERAL METHOD OF PREPARATION OF NITROGEN CONTAINING ACCELERATORS

A. One hundred parts of $C_{22}$-tricarboxylic acid or anhydride or of a mixture consisting of 10–90% $C_{22}$-tricarboxylic acid and 90–10% tall oil fatty acid or rosin are placed in a tri-necked flask equipped with stirrer, thermometer and Dean Stark trap to collect condensate. The content of the flask is heated to 140°–150° C. and 10–30 parts polyalkylene polyamine (the amount is dependent on the molecular weight of the polyamine and on the composition of the carboxylic acid mixture) is added slowly through a dropping funnel. It is heated to 220°–240° C. until all the distillate was collected.

B. $C_{22}$-tricarboxylic acid is replaced by $C_{21}$-dicarboxylic acid. The reaction procedure is as under A.

C. Polyalkylene polyamines are replaced by reaction products of polyalkylene polyamines with monocarboxylic acids (imidazolines, amido amines) or fatty amines (primary, secondary) and fatty propane diamines. Ten to 100 parts of these nitrogen compounds are reacted with 100 grams of polycarboxylic acid or polycarboxylic acid/monocarboxylic acid blends.

D. $C_{21}$-dicarboxylic acid or $C_{22}$-tricarboxylic acid (anhydride) is replaced by fumarized or maleinized resin acids (rosin). In this case the kettle content is heated to 200°–220° C. prior to the addition of the polyalkylene polyamine or the reactants described under C.

E. Ten parts of the above described modified acids are suspended in water and enough base (sodium hydroxide, potassium hydroxide, ammonium hydroxide) is added to ensure dissolution. The pH value of the solution is adjusted to pH 10.5–12.5.

The practice of this invention may be seen in the following examples wherein the preparation of various types of accelerators and types of slurries of the invention is described.

EXAMPLE 1

This example gives the procedure for particular invention accelerators:

Accelerator A

Two hundred grams of a 60:40 blend of tall oil fatty acids and $C_{22}$-tricarboxylic acid were heated to 150° C. Thirty grams of a polyethylene polyamine blend with the average molecular weight of 140 were added through a dropping funnel and the reaction mixture was heated to 220° C. until all the distillate was collected.

Accelerator B

Two hundred grams of a 60:40 blend of tall oil fatty acids and $C_{22}$-tricarboxylic acid were heated to 150° C. and blended with 60 grams of a condensate prepared from 200 grams of tall oil fatty acids with 60 grams of the polyamine blend described above at 200° C. The reaction mixture was heated to 230° C. until all the distillate was collected.

Accelerator C

Two hundred grams of a 60:40 blend of tall oil fatty acids and $C_{22}$-tricarboxylic acid were heated to 150° C. and blended with 50 grams tallow-diamine. It was heated to 240° C. until all the distillate was collected.

Accelerator D

Two hundred grams of a 60:40 blend of tall oil fatty acids and $C_{22}$-tricarboxylic acid were heated to 150° C. Fifty-five grams of oleyl amine were added and heated to 230° C. until all the distillate was collected.

Accelerator E

Two hundred grams of rosin were heated with 30 grams of fumaric acid for three hours at 200° C. To the hot modified rosin, 23 grams of a polyethylene amine blend with the average molecular weight of 140 were added and heated to 240° C. until all the distillate was collected.

Accelerator F

Two hundred grams of a 60:40 blend of tall oil fatty acids and $C_{22}$-tricarboxylic acid were heated to 150° C. and blended with 50 grams INDULIN MQK ®, a commercial cationic emulsifier. The reaction mixture was heated to 230° C. until all the distillate was collected.

Accelerator G

Two hundred grams of a 60:40 blend of tall oil fatty acids and $C_{22}$-tricarboxylic acid were blended with bis-hexamethylene-triamine bottoms and heated to 220° C. until all the distillate was collected.

Accelerator H

Two hundred grams of fumarized rosin (described under E) were heated to 200° C. and blended with 60 grams of an amido amine condensate (described under B). It was heated to 240° C. until all the condensate was collected.

Accelerator I

Two hundred grams of a 60:40 blend of tall oil fatty acids and $C_{22}$-tricarboxylic acid were heated to 150° C. and blended with a molten condensate prepared from 200 parts rosin and 100 parts of a polyethylene polyamine blend with the average molecular weight of 140 prepared at 250° C. The reaction mixture was heated at 240° C. until all the distillate was collected.

EXAMPLE 2

A cationic aqueous bituminous emulsion was prepared employing the emulsifiers listed in Table I, below, and aggregate mixing tests with each emulsion and the invention accelerators as previously performed.

First, cationic emulsions were prepared with either 62–64% Exxon ® penetration 120/150 asphalt, 1.5 emulsifier at pH 2.0 (adjusted with hydrochloric acid) and water to make up 100% (percentages based on the weight of the emulsion).

Next, slurries were prepared by adding to one 100-gram of Camak (Georgia) granite screenings, two grams Portland cement, five grams of a 1% solution of the accelerator in water (pH 10.5–12.5) and seven grams of water and 12 grams of the cationic aqueous bituminous emulsion. The blends were mixed for 30 seconds and placed in a thickness of ⅛ inch on an asphalt mat to determine curing behavior via cohesive strength measurements. The preferred range of accelerator is from 0.02% to 0.07%, with 0.05% being optimum.

Cohesive Strength Measurement Procedure

The slurry cohesive strength of each hot specimen was determined with means of a modified ASTM D-3910 cohesive strength tester. The modified cohesive tester consists essentially of (1) a frame, (2) instrument panel, (3) pressure gauge, (4) pressure regulator, (5) 4-way air valve and (6) a double-rod air cylinder mounted vertically so that a (7) rubber faced foot when lowered by air pressure against a specimen may be manually twisted to failure by a (8) peak-reading torque wrench.

Specimens are prepared and cast in a 60 mm diameter mold. A 6 mm-deep mold is used for aggregates 100% passing the 4.75 mm (#4 or 3/16") sieve and a 10 mm-deep mold is used for aggregates 100% passing the 8 mm (5/16") sieve. The specimens are cast on 10 cm (4") squares of non-absorptive 16-pound bitumen saturated roofing felt.

The modified cohesion tester is similar to the Armak ASTM D-3910-80 machine except that it is designed for a constant regulated air supply, convenient 4-way cylinder valve to operate the cylinder at controlled rate of speed. The cylinder is larger and more rugged. The contact foot used here is a flat ¼" neoprene disc of 50–60 durometer hardness, 1-18" diameter rather than a 1"diameter plug cut from an automobile tire. The procedures used may be found in Appendix A of ISSA Technical Bulletin TB #139 12/82. The pressure exerted on the foot is 92.3% of the gauge reading. The test pressure is set at 200 kPa (28.44 psi) and the cylinder foot is lowered against the centered specimen and allowed to compact the specimen for 5 to 6 seconds. The torque meter is placed on the upper cylinder rod end and twisted by hand in a firm smooth horizontal motion through 90° to 120° of arc within 0.7 to 1.0 second. The maximum torque pointer is read and the results recorded, the foot raised and cleaned and torque pointer is reset.

A series of specimens are prepared by casting a fresh mixture into 6 mm diameter rings 6 or 10 mm thick and centered on a non-absorbent surface such as 10 cm squared of 15-pound saturating roofing felt. The number of data points during a specified time span determines, of course, the number of specimens and amount of mix required.

Peak torques are recorded at 15, 30, 60, 90 minutes and so on.

Table I shows the improved curing rate of the slurry seal when the invention accelerator is added to the mix.

TABLE I

| COHESIVE STRENGTH OF SLURRY SEAL SPECIMEN | |
|---|---|
| Emulsion: | Exxon - 120/150 Penetration Asphalt, 1.5% Emulsifier, pH 2.0 (12% applied, based on the weight of the aggregate) |
| Aggregate: | Camak (granite) |
| Mixing Aid: | 2% Portland Cement (based on aggregate) |
| Accelerator: | 0.05% (based on aggregate) |

TABLE I-continued

COHESIVE STRENGTH OF SLURRY SEAL SPECIMEN

Mixing Water: 12%

| Emulsion # | Emulsifier | Accelerator | Temperature (°F.) | Cohesive Strength (kg × cm) After | | | | |
|---|---|---|---|---|---|---|---|---|
| | | | | 15 | 30 | 45 | 60 | 90 |
| | | | | (min.) | | | | |
| 1 | INDULIN MQK-1M ® | — | 60 | 10.5 | 10.7 | 11.5 | 11.0 | |
| | | — | 72 | | 12.1 | 13.8 | 13.6 | 14.5 |
| | | Fumarized Rosin[a] | 72 | | 15.3 | 20+ | 20+ | 20+ |
| | | Fumarized Fatty Acid[b] | 71 | | 14.3 | 15.5 | 20+ | 20+ |
| | | Accelerator A | 64 | 16.6 | 20+ | 20+ | 20+ | |
| | | Accelerator B | 64 | 20+ | 20+ | 20+ | 20+ | |
| | | Accelerator C | 67 | 20+ | 20+ | 20+ | 20+ | |
| | | Accelerator D | 67 | 16.5 | 13.7 | 20+ | 20+ | |
| | | Accelerator E | 65 | 14.4 | 15.2 | 15.6 | 20+ | |
| | | Accelerator F | 64 | 12.8 | 13.4 | 20+ | 20+ | |
| | | Accelerator G | 65 | 15.7 | 20+ | 20+ | 20+ | |
| | | Accelerator H | 64 | 12.1 | 15.7 | 19.7 | 20+ | |
| | | Accelerator I | 64 | 14.2 | 15.3 | 20+ | 20+ | |
| 2 | INDULIN MQK ® | — | 60 | 12.1 | 12.0 | 12.6 | 12.6 | |
| | | — | 71 | | 12.1 | 12.7 | 13.8 | 13.6 |
| | | TOFA L-5 | 70 | | 12.3 | 12.7 | 20+ | 20+ |
| | | Accelerator B | 68 | 13.8 | 13.8 | 20+ | 20+ | |
| 3 | Fatty Acid - Polyethylene Amine Condensate | — | 66 | 15.5 | 13.3 | 16.4 | 15.6 | |
| | | Accelerator B | 66 | 18.3 | 20+ | 20+ | 20+ | |
| | | Accelerator C | | 13.7 | 20+ | 20+ | 20+ | |

[a]100 parts rosin reacted with 15 parts fumaric acid at 200° C.
[b]100 parts tall oil fatty acid reacted with 16.3 parts fumaric acid at 200° C.

EXAMPLE 3

This example was a cationic emulsion modified by incorporating a polymer latex.

The cationic bituminous emulsion was prepared as in Example 2 with the exception that 3% (based on the total weight of the emulsion) of L-258 latex manufactured by Polysar Inc. was added to the soap solution used for the preparation of the emulsion. Exxon penetration 120/150 asphalt was used for emulsification; the emulsifier concentration was 1.5%; and the pH value was 2.0. The total asphalt/latex residue was 64 percent. Mixing experiments and determination of cohesive strength were determined as in Example 2.

TABLE II

COHESIVE STRENGTH[a] OF SLURRY SEAL PREPARED WITH POLYMER LATEX EXTENDED EMULSIONS

| Emulsion # | Emulsifier | Accelerator | Temperature (°F.) | Cohesive Strength (kg × cm) After | | | | |
|---|---|---|---|---|---|---|---|---|
| | | | | 15 | 30 | 45 | 60 | 90 |
| | | | | (min.) | | | | |
| 4 | INDULIN MQK-1M | — | 72 | | 17.6 | 18.9 | 20+ | 20+ |
| | | Fumarized Rosin[b] | 69 | 14.1 | 20+ | 20+ | 20+ | |
| | | Accelerator B | 65 | 20+ | 20+ | 20+ | 20+ | |
| | | Diacid 1550 ® | 65 | 14.8 | 20+ | 20+ | 20+ | |
| | | Accelerator E | 69 | 16.7 | 17.6 | 20+ | 20+ | |
| | | Accelerator A | 69 | 14.1 | 20+ | 20+ | 20+ | |

[a]Two parts cement, 0.05 part accelerator, 11 parts water and 12 parts emulsion were used per 100 parts aggregate; mixing time was 30 seconds.
[b]100 parts of rosin were reacted with 15 parts fumaric acid at 200° C.

TABLE III

COHESIVE STRENGTH OF SLURRY SEAL SPECIMEN

| Emulsion: | Exxon - 120/150 Penetration Asphalt, 1.5% Emulsifier pH 2.0 (12% applied based on the weight of the aggregate) |
|---|---|
| Aggregate: | Camak (granite) |
| Mixing Aid: | 2% Portland Cement (based on the aggregate) |
| Mixing Water: | 11% |

| Emulsion # | Emulsifier | Accelerator | % Dosage | Temp. (°F.) | Cohesive Strength (kg × cm) After | | | |
|---|---|---|---|---|---|---|---|---|
| | | | | | 15 | 30 | 45 | 60 |
| | | | | | | | (min.) | |
| 4 | Fatty Acid- Polyethylene Amine Condensate | — | — | 66 | 15.5 | 13.3 | 16.4 | 15.6 |
| | | Accelerator A | 0.05 | 66 | 18.3 | 20+ | 20+ | 20+ |
| | | Accelerator J[a] | 0.01 | 70 | 12.1 | 14.8 | 17.9 | 20+ |
| | | Accelerator J[a] | 0.02 | 67 | 15.7 | 20+ | 20+ | 20+ |

TABLE III-continued

COHESIVE STRENGTH OF SLURRY SEAL SPECIMEN

| | | | | | | |
|---|---|---|---|---|---|---|
| Accelerator J[a] | 0.05 | 66 | 15.6 | 20+ | 20+ | 20+ |

[a]Accelerator J: One hundred grams of a 69:40 blend of tall oil fatty acid and $C_{22}$-tricarboxylic acid were heated and blended with 100 grams of a polyethylene amine blend with the average molecular weight of 140. It was heated to 220° C. until all the distillate was collected. After cooling to 150° C., 400 grams of a 60:40 blend of tall oil fatty acid and $C_{22}$-tricarboxylic acid were added and heated to 240° C. until all the distillate was collected.

Table III shows the efficiency of the Accelerator J at low dosage.

TABLE IV

COHESIVE STRENGTH OF SLURRY SEAL SPECIMEN

| Emulsion: | Edgington Hard Base Asphalt, 1.25% Emulsifier (INDULIN MQK-1M*), pH 2.0 (14% applied based on the weight of the aggregate) |
|---|---|
| Aggregate: | Camak (granite) |
| Mixing Aid: | 1% Portland Cement (based on the aggregate) |
| Mixing Water: | 12% |

| Emulsion # | Emulsifier | Accelerator | % Dosage | Temp. (°F.) | Cohesive Strength (kg × cm) After | | | |
|---|---|---|---|---|---|---|---|---|
| | | | | | 15 | 30 | 45 | 60 |
| | | | | | | | (min.) | |
| 5 | Modified Fatty Acid-Polyethylene Amine Condensate* | — | — | 45 | 10.6 | 17.5 | 17.9 | 20.6 |
| | | — | — | 63 | 19.0 | 23.3 | 17.3 | 22.4 |
| | | — | — | 81 | 11.7 | 21.8 | 20+[a] | 20+[a] |
| | | Accelerator K[b] | 0.025 | 45 | 20.3 | 20+[a] | 20+[a] | 20+[a] |
| | | Accelerator | 0.05 | 45 | 20+[a] | 20+[a] | 20+[a] | 20+[a] |

[a]Test specimen stayed intact after the application of the cohesion test, indicating sufficient strength to support traffic.
[b]Accelerator K: Sixty-seven grams of $C_{21}$-dicarboxylic acid (Diacid ® 1550) were heated to 150° C. and mixed with 10 grams aminoethyl piperazine. It was further heated to 250° C. until all distillate was collected.

Table IV shows the efficiency of Accelerator K at extreme low paving temperatures.

While the invention has been described and illustrated herein by references to various specific materials, procedures, and examples, it is understood that the invention is not restricted to the particular materials, combinations of materials, and procedures selected for that purpose. Numerous variations of such details can be employed, as will be appreciated by those skilled in the art.

We claim:

1. An improved process for preparing a paving slurry seal mixture of a cationic aqueous bituminous emulsion and mineral aggregate capable of being worked comprising mixing a densely graded mineral aggregate passing through No. 4 and at least 80% retained on 200 mesh screen, and from about 4% to about 16% water, based on the weight of the mineral aggregate, containing up to 3% of an inorganic additive to reduce the setting time of the mixture to prewet the aggregate, and mixing the prewetted aggregate with from about 8% to about 20% of an oil in water type emulsion, based on the weight of the mineral aggregate, wherein the emulsion is comprised of from about 30% to about 80% bitumen, based on the weight of the emulsion, from about 0.1% to about 10% of a cation-active emulsifier based on the weight of the emulsion, wherein the emulsifier is selected from the group consisting of reaction products of a polyamine with polycarboxylic acids and anhydrides of the general formulae

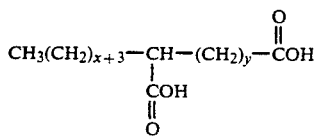

-continued

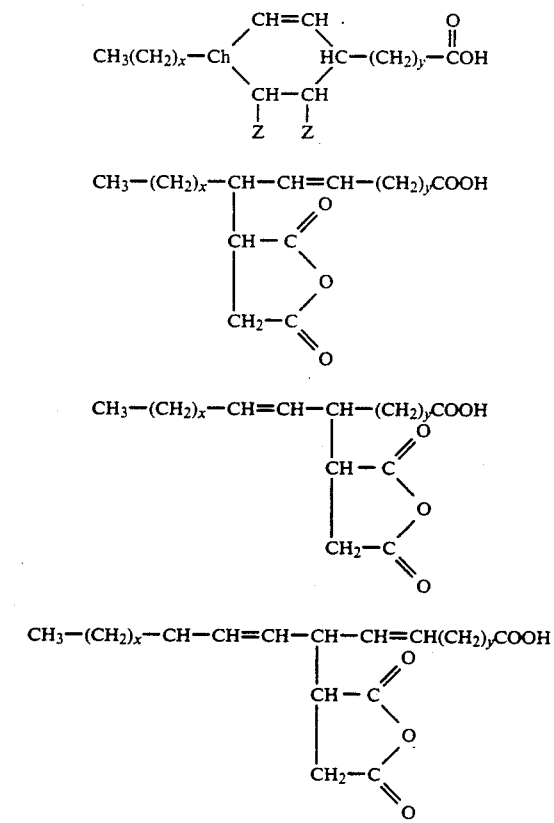

-continued

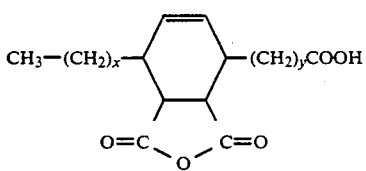

wherein x and y are integers from 3 to 9, x and y together equal 10-14, at least one Z is a carboxylic acid group and any remaining Z is hydrogen, and water to make up 100% by weight of the emulsion, the emulsion having a pH in the range of from 2-7, wherein the improvement comprises adding to the aggregate prewet water from 0.02% to 0.07%, based on aggregate, of one or more additives selected from the group consisting of tall oil fatty acids, said polycarboxylic acid, fumarized or maleinized rosin, a polyamine condensate formed by the reaction product of a lesser molar amount of a polyamine with a greater molar amount of said polycarboxylic acid; and the polyamine condensate post-reacted with fumarized or maleinized rosin to give cationic bituminous emulsions of reduced cure times.

2. The improved process of claim 1 wherein the paving slurry seal mixture is cured at a temperature below 75° F.

3. The improved process of claim 1 wherein the reaction product of a lesser molar amount of a polyamine with a greater molar amount of said polycarboxylic acid is prepared by reacting an excess of polycarboxylic acid with a member of the group of polyamines consisting of fatty amines, fatty propane diamines, fatty amidoamines and fatty imidazolines.

* * * * *

UNITED STATES PATENT AND TRADEMARK OFFICE
CERTIFICATE OF CORRECTION

PATENT NO. : 5,178,674
DATED : January 12, 1993
INVENTOR(S) : Peter Schilling et al It is certified that error appears in the above-indentified patent and that said Letters Patent is hereby corrected as shown below:

On the cover page, insert --Related U.S. Application Data Continuation-in-part of Ser. No. 446,809, Dec. 6, 1989, now U.S. Pat. No. 5,096,495, which is a divisional of Ser. No. 322,916, Mar. 14, 1989, now abandoned.

In column 1, lines 6 and 7, delete "co-pending".

In column 1, line 8, delete "5,046,495" and substitute therefor --5,096,495--.

In column 2, line 15, delete ";advantage" and substitute therefor --advantage--.

In column 2, line 62, after traffic, delete "," and substitute therefor --.--.

In column 2, line 64, after desired, insert --.--.

In column 3, line 24, delete "cationactive" and substitute therefor --cation-active--.

UNITED STATES PATENT AND TRADEMARK OFFICE
CERTIFICATE OF CORRECTION

PATENT NO. : 5,178,674
DATED : January 12, 1993
INVENTOR(S) : Peter Schilling et al It is certified that error appears in the above-indentified patent and that said Letters Patent is hereby corrected as shown below:

In column 3, second formula, delete "$CH_3(CH_2)_x-Ch$" and substitute therefor --$CH_3(CH_2)_x-CH$--.

In column 3, fifth formula, delete "$CH_3-(CH_2)_x-CH-CH$" and substitute therefor --$CH_3-(CH_2)_x-CH$--.

In column 5, line 14, after surface, insert --.--.

In column 5, line 66, after group, insert --.--.

In column 7, line 39, delete "aminoethylipiperazine" and substitute therefor --aminoethylpiperazine--.

In column 8, line 44, after $C_2H_5-$, insert --$C_3H_7-$,--.

In column 11, line 4, after conditions, delete "," and substitute therefor --.--.

In column 11, line 7, delete "rowel" and substitute therefor --towel--.

UNITED STATES PATENT AND TRADEMARK OFFICE
CERTIFICATE OF CORRECTION

PATENT NO. : 5,178,674
DATED : January 12, 1993
INVENTOR(S) : Peter Schilling et al It is certified that error appears in the above-indentified patent and that said Letters Patent is hereby corrected as shown below:

In column 11, line 42, after phenol, delete ","
and substitute therefor --.--.

In column 12, line 1, after 75°F. delete ",".

In column 17, line 1 of footnote a), delete "69:40"
and substitute therefor --60:40--.

In column 17, after formula, insert --or--.

In column 18, first formula, delete "$CH_3(CH_2)_x$-Ch"
and substitute therefor --$CH_3(CH_2)_x$-CH--.

In column 18, fourth formula, delete "$CH_3-(CH_2)_x$-CH-CH"
and substitute therefor --$CH_3-(CH_2)_x$-CH--.

Signed and Sealed this

Sixteenth Day of November, 1993

Attest:

BRUCE LEHMAN

*Attesting Officer*      *Commissioner of Patents and Trademarks*